(12) United States Patent
Kelley et al.

(10) Patent No.: US 6,958,216 B2
(45) Date of Patent: Oct. 25, 2005

(54) DNA-BRIDGED CARBON NANOTUBE ARRAYS

(75) Inventors: Shana O. Kelley, Boston, MA (US); John Fourkas, Chestnut Hill, MA (US); Michael Naughton, Norwood, MA (US); Zhifeng Ren, Newton, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 10/042,911

(22) Filed: Jan. 9, 2002

(65) Prior Publication Data

US 2002/0172963 A1 Nov. 21, 2002

Related U.S. Application Data

(60) Provisional application No. 60/260,758, filed on Jan. 10, 2001.

(51) Int. Cl.[7] .............. C12Q 1/68; C12M 1/00; G01N 15/06; C07H 21/04
(52) U.S. Cl. .............. 435/6; 435/7.1; 435/174; 435/283.1; 435/287.2; 422/68.1; 422/82.01; 536/23.1; 536/24.3; 977/DIG. 1
(58) Field of Search .............. 435/6, 7.1, 174, 435/293.1, 287.2, 283.1; 422/68.1, 82.01; 536/23.1, 24.3

(56) References Cited

U.S. PATENT DOCUMENTS

| | | | |
|---|---|---|---|
| 5,866,434 A | 2/1999 | Massey et al. | 436/526 |
| 6,062,931 A | 5/2000 | Chuang et al. | 445/24 |
| 6,146,227 A | 11/2000 | Mancevski | 445/24 |
| 6,159,742 A * | 12/2000 | Lieber et al. | 436/164 |
| 6,399,303 B1 * | 6/2002 | Connolly | 435/6 |
| 6,400,091 B1 * | 6/2002 | Deguchi et al. | 315/169.1 |
| 6,506,564 B1 * | 1/2003 | Mirkin et al. | 435/6 |
| 6,656,693 B2 * | 12/2003 | Saraf et al. | 435/6 |

FOREIGN PATENT DOCUMENTS

WO     WO 98/05920     * 2/1998

OTHER PUBLICATIONS

Burghard, et al.; "Controlled Absorption of Carbon Nanotubes on Chemically Modified Electrode Arrays"; *Adv. Mater.*; (1998); vol. 10 No. 8, pp. 584–588.

International Search Report, International Application No.: PCT/US02/00645; dated Aug. 28, 2002.

* cited by examiner

*Primary Examiner*—BJ Forman
(74) *Attorney, Agent, or Firm*—Palmer & Dodge, LLP; Paula Campbell Evans; David J. Dykeman

(57) ABSTRACT

A class of biological sensing devices that include a substrate comprising an array of carbon nanotubes (CNTs) to which are chemically attached biological molecules is disclosed. The attached biological molecules are capable of electrical conductivity that is responsive to chemical changes occurring as a result of their interaction with target species. A means for means for using DNA as a material of potential in molecular electronic sensor devices, being primarily based on molecular electron-transfer reaction processes between DNA-binding donors and acceptors is also disclosed, including composition, method of manufacture and their use are described.

42 Claims, 18 Drawing Sheets

S-GAAGCATTAACGAGTTACTCAATGAGTCTTTTAATGCCAGGTTCTATACCG-S
(SEQ ID NO: 1)

↓ 50 nucleotide anthrax marker sequence (SEQ ID NO: 1)
S-GAAGCATTAACGAGTTACTCAATGAGTCTTTTAATGCCAGGTTCTATACCG-S
CTTCGTAATTGCTCAATGAGTTACTCAATGAGTTACTCAGAAAATTACGGTCCAAGATATGGC
(SEQ ID NO: 2)

increased conductivity

⇒⇒⇒ sequence obtained from innocuous strains/species target sequence obtained from bacterial cultures
CTTCGTAATTGCTCAATGAGTTACTCAATGAGTTACTCAGAAAATTACGGTCCAAGATATGGC
(SEQ ID NO: 2)

FIG. 16

SEQUENCE LISTING

<160> NUMBER OF SEQ ID NOS: 2

<210> SEQ ID NO 1
<211> LENGTH: 51
<212> TYPE: DNA
<213> ORGANISM: Artificial
<220> FEATURE:
<223> OTHER INFORMATION: Synthetic complimentary sequence to Bacillus
      anthracis

<400> SEQUENCE: 1
gaagcattaa cgagttactc aatgagtctt ttaatgccag gttctatacc g       51

<210> SEQ ID NO 2
<211> LENGTH: 51
<212> TYPE: DNA
<213> ORGANISM: Bacillus anthracis

<400> SEQUENCE: 2
cttcgtaatt gctcaatgag ttactcagaa aattacggtc caagatatgg c       51

DNA-BRIDGED CARBON NANOTUBE ARRAYS

This application claims priority to Provisional U.S. Application Ser. No. 60/260,758 filed on Jan. 10, 2001.

FIELD OF THE INVENTION

The present invention relates to carbon nanotube devices. More particularly, it relates to carbon nanotube chemical and biological sensor devices.

BACKGROUND OF THE INVENTION

The ability to detect chemical and biological species rapidly with specificity and at very low concentrations is becoming increasingly important, particularly in the medical, environmental and forensic areas Detection of low levels pathogenic species such as agents that pose a biological threat, for example, provides a crucial measure of environmental contamination by such agents since their existence, even at low concentrations, can have serious pathological consequences. Sensitive detection devices therefore, enables the elimination of such pathogens prior to their causing significant harm. There is also a growing need for the rapid and quantitative detection of biological species in a number of biomedical applications, and the healthcare and food industries.

Chemical sensors disclosed in the art commonly utilize solid semi-conductor materials such as metallic oxides as sensor probes. Detection of target species by these sensors is typically accomplished by measuring a change in electrical resistance or optical property of the probes caused by adsorption of the species on the probe material surface. To provide adequate sensitivity however, such sensors have to operate at elevated temperatures to cause an increase in chemical reactivity of the target species to the probe surface. Other limitations of prior art probes include long recovery times, poor specificity and reproducibility, and their inability to be specifically adapted for detection of a wide range of chemical and biological species.

Biological sensing devices offer the potential for providing high a degree of specificity and good sensitivity, but remain largely unexplored due to technical and chemical issues pertaining to their structure-property characterization. Although charge transport properties of certain macromolecules such as DNA have been studied, their application as sensors has not been explored. This may be attributed to the inadequate understanding of the nature of the intrinsic properties of DNA, which has proven difficult to study directly using presently available systems.

Nanotechnological approaches to molecular electronics ("molectronics") although theoretically feasible for sensor applications on the other hand, has not been practically realized mainly because they require materials with programmable structural and electronic characteristics.

In view of the above, there is a need for sensing devices that provide a highly sensitive and specific response to target species requiring detection, but more desirably, provide a tunable response to a variety of chemical and biological species that pose pathological hazards to the environment.

OBJECTS AND SUMMARY OF THE INVENTION

The present invention comprises biological sensing devices that include a substrate comprising an array of carbon nanotubes (CNTs) grown on a catalyst material deposited on the surface of a non-metallic material, to which are chemically attached biological molecules. The attached biological molecules are capable of electrical conductivity that is responsive to chemical changes occurring in said molecules as a result of their interaction with target species that they are designed to "sense" and detect. In particular, the invention biosensors based on the intrinsic property of electrical conduction present in nucleic acids such as DNA and RNA and methods for fabricating them.

The present invention provides a means for using DNA as a material of potential in molecular electronic sensor devices, being primarily based on molecular electron-transfer reaction processes between DNA-binding donors and acceptors. The π-stacked array of aromatic heterocycles at the core of the double-helical structure of DNA mediate strong electronic coupling between bound molecules. The integrity of the base stack of DNA is critical for efficient charge transport, as the presence of disruptions in π-stacking brought about by mis-paired bases or unpaired bases, and other external factors that perturb the base stack severely attenuates DNA-mediated reactions. Unlike conventional methods of monitoring the intrinsic electrical properties of DNA using conductivity measurements that are inconsistent, and wherein neither variation of the length or sequence of the DNA, nor the points of electrical contact along the DNA helix are well-defined, the present invention provides a means of measuring the conductance of synthetic DNA assemblies, and their incorporation into molecular electronic devices.

The present invention also provides methods for incorporating DNA assemblies synthetically into molecular electronic devices and for measuring their electrical conductivities. Using nanofabrication techniques, three-dimensional CNT arrays capped with gold are constructed on a surface and subsequently functionalized chemically with DNA molecules. The ability to "wire" sequences of synthetically defined composition chemically into nanoelectrodes, enables systematical address, at an unprecedented level of detail, based on the influence of DNA structure, sequence, and length on conduction. The sensor devices of the invention utilize the capability of double-stranded DNA to conduct electricity, provides the means to measure the electrical conductivity, and more importantly, changes in electrical conductivity in short (<100 bp) and specific DNA sequences. Sensors of substantially high sensitivity and portability are therefore obtainable. The ability to measure extremely small changes in electrical conductivity in the sensors of the invention is superior to conventional methods used for detecting DNA sequences employing optical methods, such as by laser confocal fluorescence microscopy, thereby rendering them suited for detection and quantitation of extremely low levels of the target species. Furthermore, the sensors of the invention are adaptable to conventional silicon chip technology, whereby sensing can performed off the chip surface. The extra-surface detection in the sensor devices of the invention is achieved by precise placement of electrically conducting CNTs on lithographically-prepared substrates, wherein electrical connections between pairs of carbon nanotubes is completed by target DNA strands complementary to probe DNA strands that are previously set in place. Electrical connectivity between the CNTs and the DNA molecules is achieved via the directed-assembly of DNA molecules onto gold coated CNT's via thiol linkers. Sensors of the present invention have the ability to detect ultra-low levels of a variety of biologically relevant pathogens in air, soil and water samples, and may be configured as a miniaturized, portable device.

The present invention also provides a means for measurement of electrical conductivity of DNA in sensors containing it, and enables the detection of specific DNA sequences, such as those belonging to pathogenic target species. Such pathogen DNA sensors of the invention comprise of DNA circuits wherein nanoscale electrical leads are constructed by incorporating individually addressable multi-walled CNTs. A critical aspect of this design involves the attachment of a metallic gold layer (either as a spherical nanoparticulate or as a coating) to the tips of the individual nanotubes provide an anchoring surface for the DNA molecules. The gold surface on the nanotube tips enables the immobilization of thiol modified DNA sequences via spontaneous self-assembly. The sensors of the invention comprise of an array of pairs of closely-spaced, individually electrically addressable CNTs comprising a terminally capped metallic gold layer on their terminal ends. Pathogen sensors of the invention include DNA circuits functioning as nanoscale electrical leads comprising individually addressable multi-walled CNTs. A critical aspect in the sensor design involves the attachment of one or more gold layers either as a coating or as a nanosphere particle to the tips or terminal ends of the nanotubes which act as intermediaries between the nanotubes and the DNA molecules. The introduction of a gold surface facilitates the immobilization of DNA sequences by self-assembly. Attached to each sphere in a pair of CNTs will be multiple copies of a particular sensor strand. Introduction of DNA that is complementary to the sensor strands on adjacent CNTs, causes an electrical connection to be formed between the nanotubes. A complete sensor device of the invention has a library of sensor sequences that are either individually or in specific groups unique to particular targets, such as for example, pathogens. Since each pair of nanotubes can potentially be bridged by multiple strands of duplex DNA, the total conductivity depend on the concentration of DNA complementary to the sensor strands. Thus, the device of the invention can be used for the rapid detection, fingerprinting, and quantitation of DNA from pathogenic organisms.

The present invention utilizes previously known nanofabrication techniques to obtain three-dimensional CNT arrays capped with gold nanospheres that can be chemically functionalized with DNA. The ability to "wire" sequences of synthetically defined compositions of DNA chemically into nanoelectrodes enables systematical addressing at unprecedented levels of detail, and enables the monitoring of the influence of DNA structure, sequence, and length on electrical conductivity. The CNT-based arrays of the invention therefore, provide well-defined systems for inducement of electrical conductivity in DNA, and establish the extent to which DNA can serve as "molecular wiring" in nanoscale electronic devices. Regardless of the absolute conductivity of DNA molecules, conductivity can be modulated through sequence and structural effects. This allows for the properties of DNA, which are amenable to extensive synthetic manipulation, to be exploited to their fullest potential.

The sensor attribute of the present invention relies on the sensitivity of DNA-mediated charge transport to base stacking. Since single-stranded DNA has a considerable amount of structural freedom, the stacking in such a molecule should not promote electrical conductivity; only the substantially more rigid, double-stranded DNA molecules are capable of conducting electricity. Thus, if a single-stranded DNA molecule is used as a molecular wire between two electrical contacts, no conductivity would be measurable unless until a complementary strand of DNA hybridizes to the single strand to form a conductive duplex. Since only complete hybridization with a sensor strand results in electrical conductivity, the single strand of DNA that "wires" together two electrical CNT contacts forms an extremely sensitive and highly selective electrical sensor. Alternatively, a complementary strand can be used to link two initially unattached sensor strands to form a single, conductive duplex in a system in which no conductivity is possible. This results in enhanced sensitivity, since the conductivity of a DNA molecule is substantially higher than that of a vacuum. A measurable response is therefore obtainable with such configurations that is independent of the intrinsic conductivity of DNA.

The use of CNT arrays as a structural support for the DNA based sensor devices of the invention is essential to the "sensing" attribute of the device. The measurement of electrical conductivity requires that only the ends of sensor DNA strands be in contact with the electrical leads. By immobilization of DNA probe sequences on gold spheres attached to CNTs, short-circuiting resulting from contact between intervening regions of the DNA bridge and the electrode surface is minimized. The use of a three-dimensional array of CNTs will also orient the resultant sensor probe sequences of the invention favorably (head-to-head) for hybridization with an incoming target sequence, and offers a distinct advantage over conventional metal nanoelectrode flat arrays which cannot present incoming sequences with such an orientation. The DNA immobilized CNT arrays of the invention can be used for fabricating electrically addressable DNA chips, for incorporation into electrical DNA biosensors with high-throughput capability.

The DNA sensor arrays of the invention are also compatible with conventional technologies for fabricating electrically conducting nanocircuits, such as etched trenches in silicon or surface deposition of thick nanowire contacts. The utilization of CNTs as electrical leads and "off-surface" supports for the sensor arrays of the present invention however, provides several advantages over these conventional methods. In the trench version, etch grooves may employed to form a trench beneath and between the ends of two surface-deposited nanowires, with these now partly suspended ends subsequently linked by conducting DNA strands. However, this process is unreliable and complex, with poor uniformity of the electrode gap, and severe problems with the nanoscale etching. Using thick electrodes for isolation of the DNA contacted region from the surface, on the other hand introduces problems such as difficulty in obtaining (and maintaining) electrode gaps of the right magnitude (~10 nm) as the metal electrode thickness increases. Such limitations may be overcome by using methods that produce electrode gaps on the sub-10 nm scale using a combined electromigration/break-junction technique. Non-uniform gaps that are separated from the substrate by only 10–15 nm. The present invention uses electron beam lithography and lift-off to produce reliably electrodes with separation gaps under 10 nm. The method of the invention allows to reproducibly prepare sets of nanoelectrodes with sub-10 nm gaps (vide infra) (down to 6 nm if required), and then grow CNTs at the ends of these electrodes to any height desired. DNA strands will then link the tops of these CNTs.

It is a principal object of the present invention to provide chemical and biological sensor devices that are capable of rapid and specific detection of extremely low levels of chemical and biological agents, particularly agents that pose a pathogenic hazard to the environment.

It is another object of the invention to provide a method for fabricating a new class of biosensors based on an intrinsic property of nucleic acids, namely, their electrical conduction.

It is another objective of the invention to provide synthetic assemblies of electrically conducting nucleic acids, including DNA assemblies, on a substrate surface, and their incorporation in molecular electronic devices using a nanofabrication technique so as to enable them to behave as molecular conductors in sensing applications.

It is another object of the invention to provide a method for anchoring nucleic acids on a substrate surface and rendering to be electrically conducting, thereby enabling use in molecular electrical circuits.

It is yet another object of the invention to provide carbon nanotube arrays substrate for anchoring nucleic acid substrates including DNA via chemical bonding.

It is a further objective of the invention to provide carbon nanotube arrays wherein at individual nanotubes are at least partially coated with a metallic material which enables anchoring of nucleic acid molecules.

It is also an object of the invention to provide electrically nanoelectrical circuits containing nucleic acid anchored CNT arrays that are deposited on a semiconducting material, methods for their fabrication.

It is also an object of the invention to provide a method for the detection chemical and biological species using the sensors of the present invention.

These and other objects may be accomplished by a method for adsorbing nucleic acids on to the surface of metallic layer such as gold that is deposited either as a coating or as a metallic particle on individual nanotubes of a CNT array, that includes the steps of thiolating the nucleic acid and depositing the thiolated nucleic acid on the gold coated CNT array for a sufficient time for formation of covalent chemical bonds between the sulfur and the gold. The CNT substrates may be obtained growing CNT arrays on a catalyst containing surface by plasma-enhanced hot filament vapor deposition. The catalyst containing surface for CNT growth can be patterned on a material surface by e-beam so as to produce CNT "nanocircuits." As used herein, the term nucleic acid pertain to both DNA and RNA which may be used interchangeably, because the invention is applicable to thiolation and attachment of both molecules to gold coated CNTs. By "thiolation" is meant the incorporation of a thiol or mercapto (SH) group by chemical derivatization of the nucleic acid to give the corresponding thiolated nucleic acid Nu-SH, and enabling their subsequent attachment to the gold coating on the CNT arrays by formation of Au—S-Nu type covalent bonds.

BRIEF DESCRIPTION OF THE FIGURES

FIG. 16 shows the detection process of anthrax genomic sequences by monitoring DNA conductivity.

DETAILED DESCRIPTION

Figure 1:
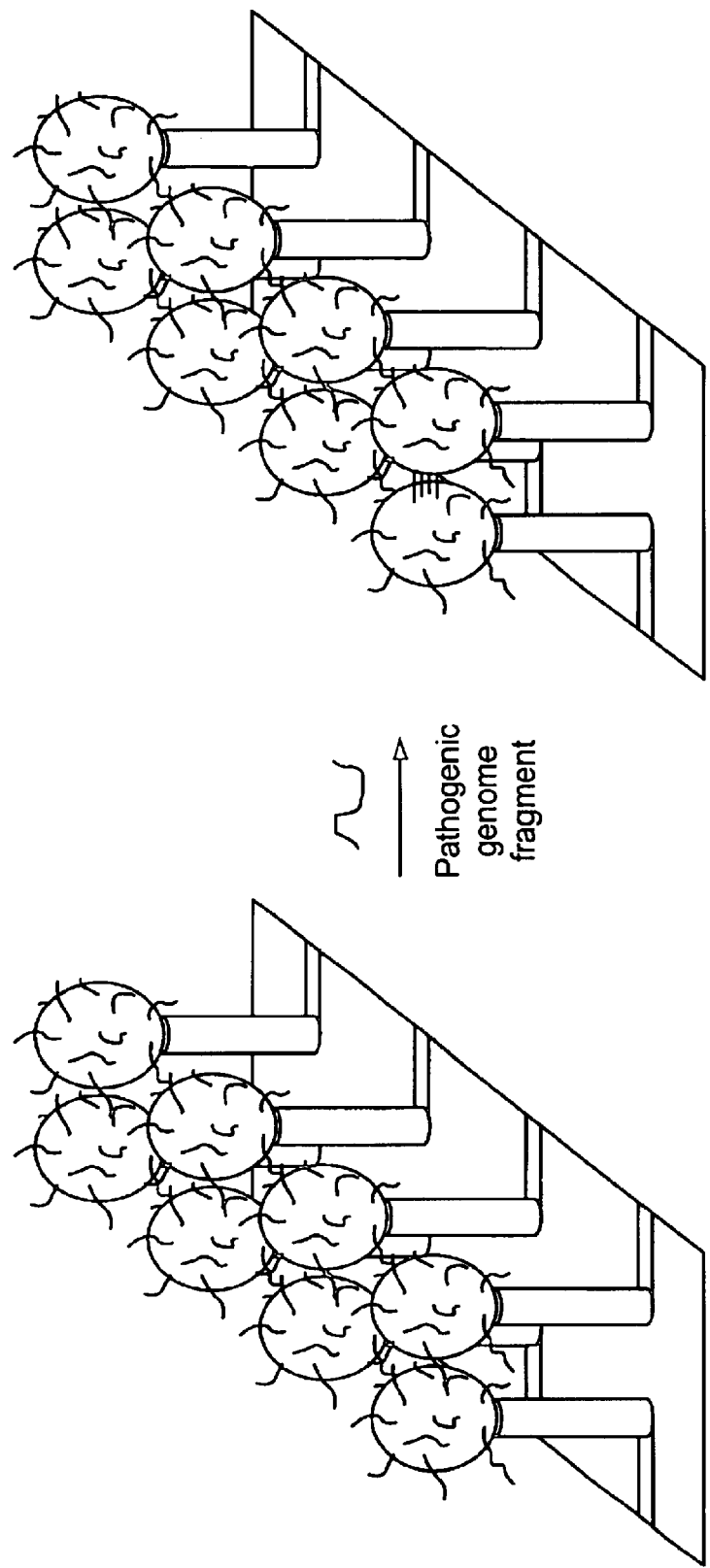
FIG. 1 shows a schematic depiction of the DNA containing CNT "sensor" array of the invention. DNA "sensor" sequences are bound to particulate gold spheres at the tips of electrically addressed CNTs. Complementary DNA strands from a pathogenic genome fragment (target species) complete a circuit between adjacently paired nanotubes.

The fabrication of DNA-based electrical circuits of the invention comprising self-wiring DNA sensor arrays (shown in FIG. 1) utilizes the following four distinct steps:

1) Controllable Creation of Arrays of Addressable Multi-walled Carbon Nanotubes

Arrays of paired, aligned CNTs, with nanotube proximity of about 100 nm in each pair are grown on a substrate surface to a length sufficient for subsequently linking them with DNA strands as described below. At least a portion of the nanotubes are individually electrically addressable. In one embodiment, multi-walled CNTs are preferred, as they are, in general, conducting (with proper chirality) and rigid. Multi-walled CNTs are grown by the plasma-enhanced hot-filament chemical vapor deposition method on a substrate. In another embodiment, the substrate is an e-beam patterned substrate.

2) The Fabrication of Smooth, Gold-coated Spheres of Controllable Dimension.

Figure 2:
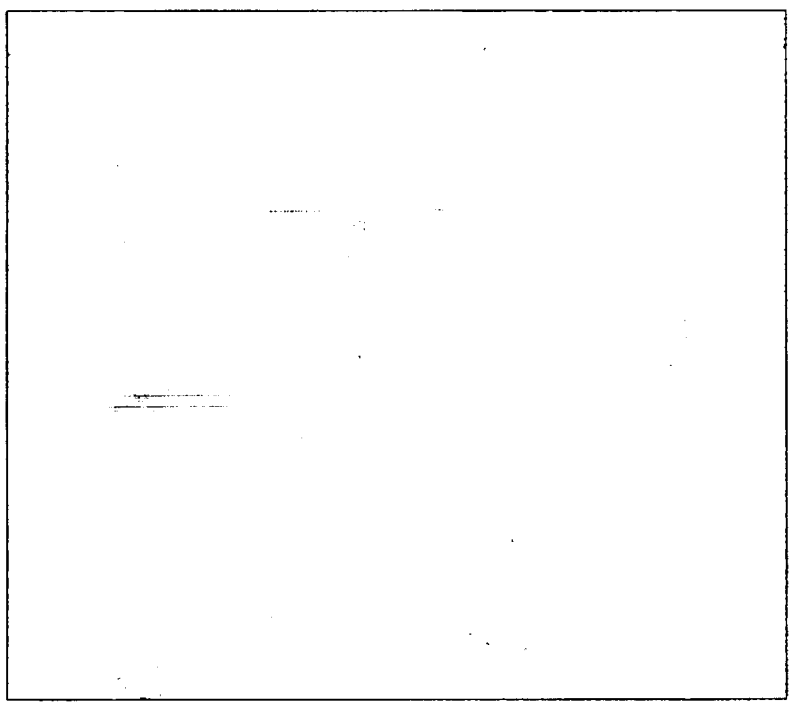
FIG. 2 shows Au-coated polymer microspheres.

The present invention discloses a method that allows for the fabrication of smooth, gold-coated spheres of controllable diameters that range from about 100 nm to about hundreds of μm. FIG. 2 shows the micron-scale gold-coated spherical beads prepared by this method.

(3) The Self-assembly of Gold Particles onto the Ends of Functionalized Nanotubes.

The nanotube ends in CNT arrays are selectively etched by a combination of nitric and sulfuric acid treatments. The etching process converts the carbon atoms on the ends of the tubes into carboxylic acid groups, which can then be reacted with amine-containing molecules to place any functionality desired at the tips of the tubes. For purposes of self-assembly, conductive, thiol-containing molecules are attached to the carboxylic acid groups, after which gold-coated particulates (such as the beads) can be self-assembled onto the tips of the tubes. This method of the invention enables the attachment of gold nanoparticles to single-walled CNTs, and can be utilized for the attachment of larger gold spheres to multi-walled tubes.

(4) The Self-assembly of DNA onto Gold Surfaces, and the Subsequent Ability of Assembled DNA (when Double-stranded and Defect Free) to Conduct Electricity.

DNA molecules conjugated to a thiol-terminated linker are utilized to enable self-assembly on gold surfaces. The density of molecules adsorbed may be controlled either by manipulation of solution deposition conditions or surface bias. Two different single-stranded DNA sequences can be bound to neighboring spheres, following which hybridization with a strand that is complementary to both initial strands completes the electrical circuit.

The present invention utilizes the above methods in concert, as a novel means for creating selfwiring nanocircuits. The fabrication of the CNT arrays, the preparation of the gold-coated spheres, the synthesis of DNA sequences with thiol linkers, and the assembly and wiring of the DNA arrays as described below. The methods of the invention enable (i) construction of DNA-CNT simplified arrays (first generation devices) for characterization of the electrical behavior of bound DNA in the arrays, (ii) fabrication of DNA "wires" to form electrical components (second generation devices) (iii) devices that combine wires and electrical and/or electronic components to provide functional circuits (third generation devices), and (iv) enhancement of such circuits to optimize their miniaturization (fourth generation devices).

Fabrication of Electrically-addressable Carbon Nanotube Arrays

Fabrication of addressable CNT arrays utilizes both micro- and nanolithographic preparation of CNT catalyst sites and metallic addressing wires on single crystal silicon wafers. Subsequently, growth of aligned CNTs on the catalyst surface is accomplished via hot filament, plasma-enhanced chemical vapor deposition (hereinafter referred to as PECVD). Essentially, a series of thin gold wires are defined lithographically on the silicon, wherein the inner ends of pairs of individual wires are in close proximity (~100 nm). A CNT growth catalyst (e.g., nickel (Ni) or cobalt (Co)) nanodot site is defined at these proximal ends using e-beam lithography, following which the catalyst material is deposited. The wafers are then placed in a chemical vapor deposition (CVD) chamber following which CNT growth is initiated, whereupon the CNT growth occurs only at the catalyst nucleation sites. At this stage, the gold wires are passivated using electropolymerization.

Figure 3C:
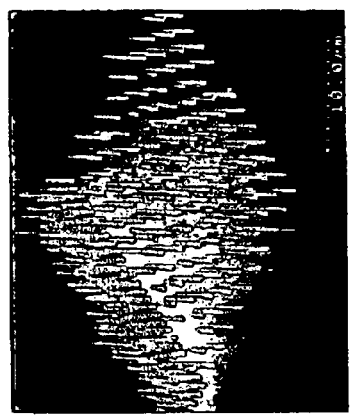
FIGS. 3 shows SEM micrographs of CNT configurations of the invention (a) relatively short, decapitated nanotubes (b) nanotubes with a diameter of about 100 nm in a lithographically-defined array and (c) a patterned array of CNT nanotubes.
Figure 3B:
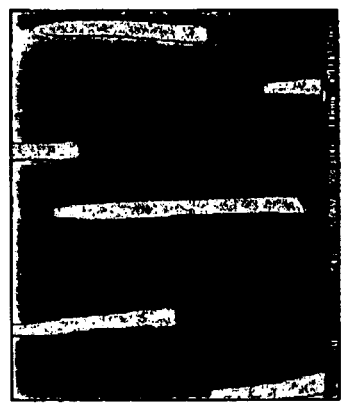
Figure 3A:
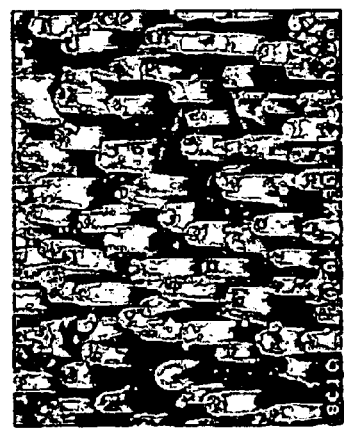
Figure 4:
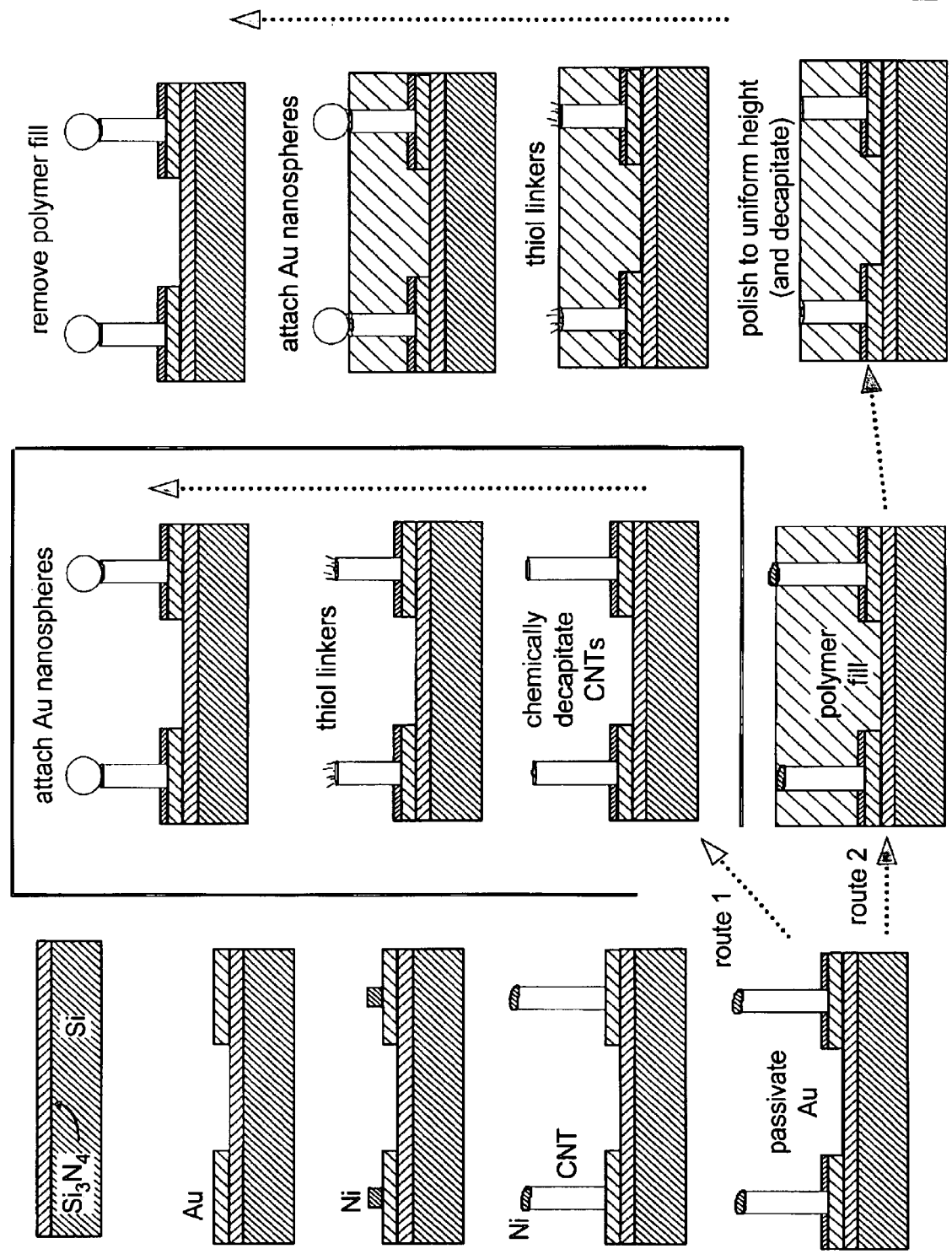
FIG. 4 shows a schematic of process for preparation of silicon substrates and growth of CNTs terminated by gold nanoparticles.

Typically, CNTs grown by this method are capped by a catalyst nanoparticle that is removable by nitric acid. The process of the invention omits the acid treatment step and thereby retaining the catalyst nanoparticle, which assists the subsequent attachment of thiol-linked gold nanoparticles, as described in C) and E) below. Additional control steps can be introduced into the process of the invention to obtain CNTs of uniform height within the arrays. Depending on growth conditions (which in turn, are dependant on properties of the catalyst), nanotubes in an array in a given growth run can vary in height between about 10% to about 50% (FIG. 3). In order to maintain height uniformity which is essential for the successful electrical linkage of CNT pairs by DNA, the polymer fill is followed by mechanical polishing steps. FIG. 4 shows the complete CNT array preparation process of the invention.

Figure 5:
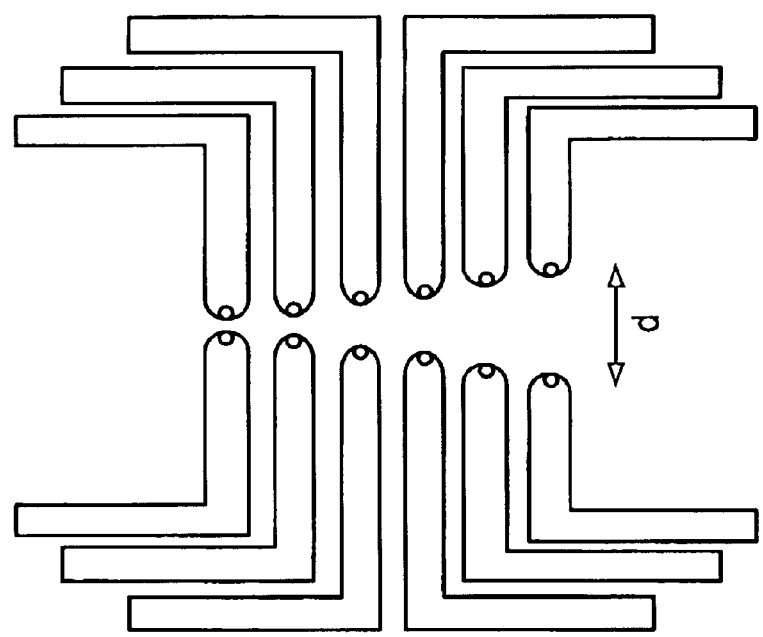
FIG. 5 shows metal leads separated by a distance d varied from −10 to −100 nm, each lead containing a Ni nanodot catalyst for growth of a multi-walled CNTs and nanotube pairs linked by complementary DNA sequences.
Figure 5:
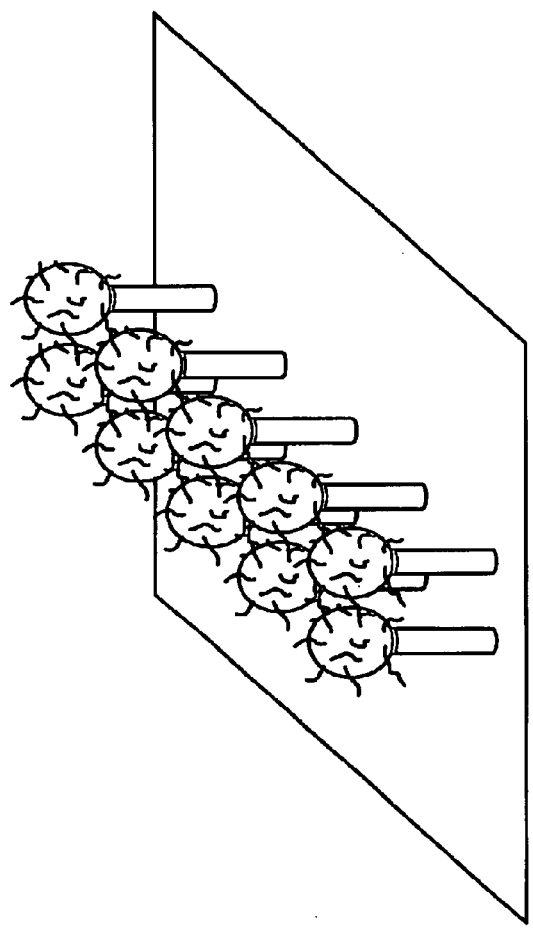

Important parameters in the process of the invention that are variable include the separation distance between pairs of wires (and therefore, between pairs of CNTs), the size (diameter and height) of the catalyst nanodot that nucleates the CNT growth and the catalyst deposition method. With a DNA base pair (bp) separation distance being of about 0.3 nm, a 100 bp sequence is about 30 nm long. Since the minimum feature size in state-of-the-art electron beam lithographic equipment is about 30 nm, a device preparation limit of 100 bp is in the acceptable range. The method of the invention can be used to grow multi-walled CNTs with nanotube diameters that are controllable down to about 100 nm. The smaller sizes required by the ~100 bp sequences of the invention can be obtained by using aligned CNT arrays of single-walled nanotubes. FIG. 5 shows nanowires with various separation gaps obtained by the process of the invention.

The method of the invention utilizes two different methods of catalyst deposition. The first one involves a conventional e-beam evaporation of metallic nickel or cobalt following an e-beam lithography step that defines the catalyst sites in an e-beam resist. This is followed by a lift-off step (of the unwanted catalyst material), leaving only the nickel or cobalt nanodots on top of the gold leads. The second method employs the self-assembly of catalyst nanoparticles from a catalyst-containing solution, which provides the advantage of eliminating the lift-off step in the process. In both cases, electrically addressable pairs of CNTs with well-defined heights and lateral separations are obtained that amenable for subsequent attachment of intermediary particles necessary for surface immobilization of DNA sequences.

C. Preparation of Gold-coated Beads

The method of the invention utilizes commercially available monodisperse, chemically-functionalized polymer spheres ("beads") with diameters as small as about 100 nm. In a preferred embodiment, amine-functionalized beads are used for gold coating. Disubstituted compounds containing both thiol and carboxylic-acid functionalities are bound chemically to the beads using amide-coupling chemistry specific for carboxylic acid groups. Subsequent immersion of the beads in a suspension of gold nanoparticles results in self-assembly of gold nanoparticles onto the bead surface. Diffusion of the nanoparticles into the beads is precluded by the relatively small pore size of the polymeric beads; the self-assembly reaction is, therefore, surface-specific. After a single layer of gold nanoparticles has been deposited on the bead surface, the gold layer can be built up by a serial repetition of the above steps. In another preferred embodiment the initial layer of gold nanoparticles can be grown to a predetermined layer thickness by electroless deposition of gold. Both processes can be used to "tune" the coated sphere diameters to a predetermined value.

Synthesis of DNA Sequences with Thiol Linkers

Figure 6A:
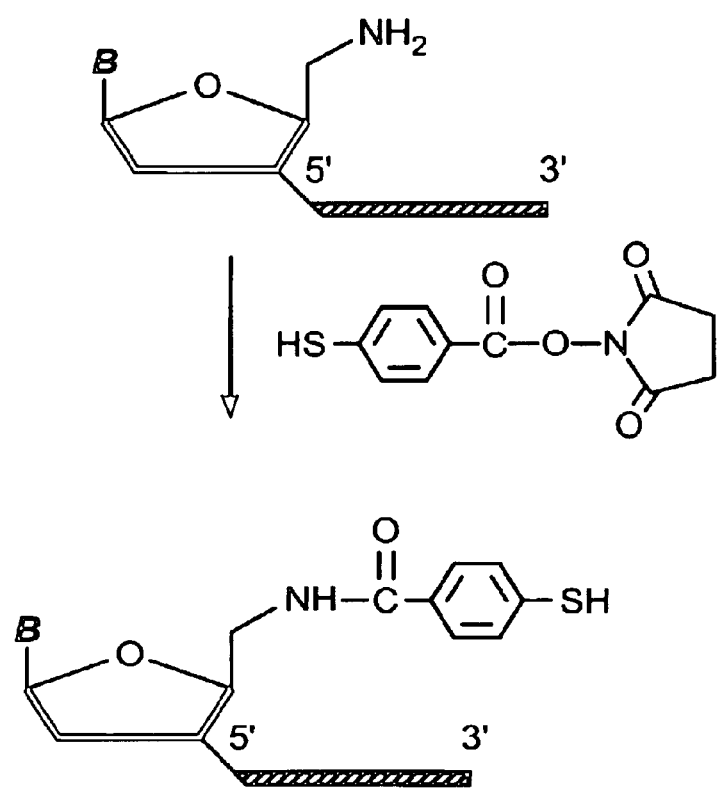
FIG. 6 shows the derivatization of DNA oligonucleotides at (a) the 5'-terminus or (b) 3'-terminus by reacting an activated derivative of 4-mercaptobenzoic acid with a 5'- or 2'-amine on the terminal ribose, respectively.
Figure 6B:
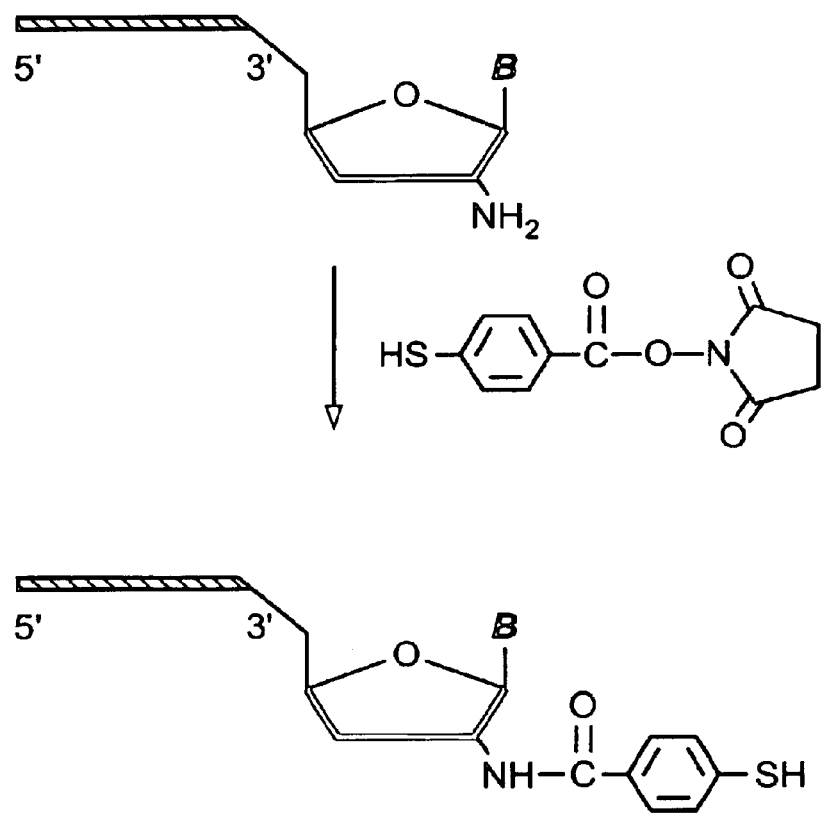
Figure 7A:
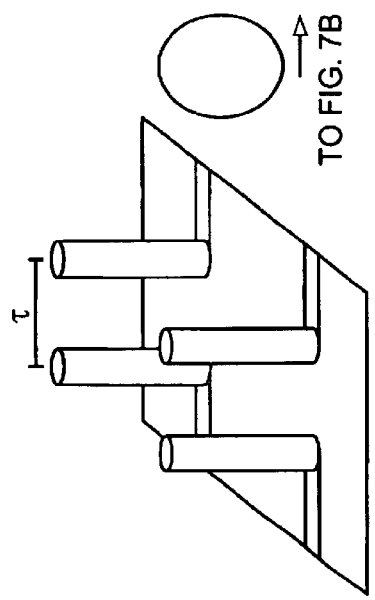
FIG. 7 shows the fabrication and wiring of DNA-CNT arrays of the invention. The ends of the electrically addressable nanotubes in the array are (a) etched and functionalized with thiols (b) Gold-coated spheres are subsequently self-assembled to the tubes and (c) DNA sequences with thiol linkers are directed to selected spheres by application of a voltage, and (c) resulting in an addressable array of gold-bound DNA sequences; (d) strands of DNA that are complementary to the sequences on adjacent spheres form a conductive path between the spheres.
Figure 7B:
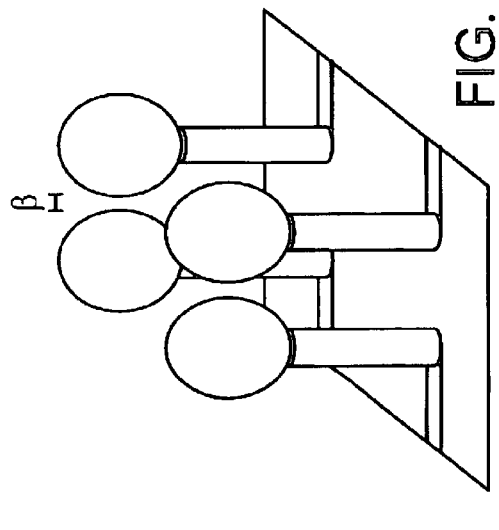
Figure 7C:
Figure 7C:
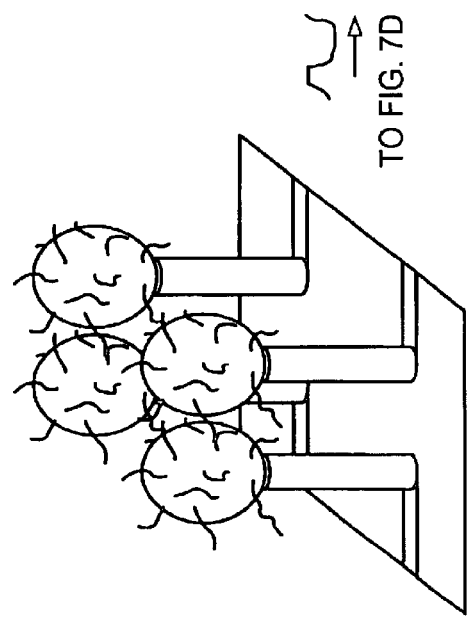
Figure 7D:
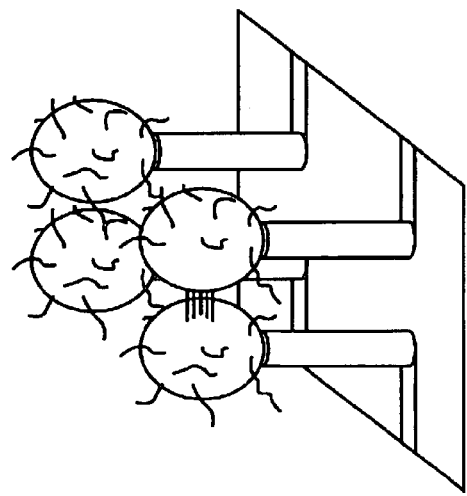

The attachment of DNA oligonucleotides to gold nanospheres by the method of the invention utilizes linkers that impart the shortest connectivity and provide the highest level of conjugation so that measured electrical conductivities correspond closely to DNA, and not to the properties of the linker. In a preferred embodiment, the coupling method involves a solution-phase reaction between 4-mercaptobenzoic acid and a terminal amine either at the 2' or 5' position on the ribose moiety (FIG. 6). This method provides a highly conjugated path between the gold particle and the DNA base stack. The incorporation of an amine at the 2' or 5' position is accomplished during chemical DNA synthesis by using commercially available reagents. A 2'-derivatization orients the DNA away from the gold surface when the linker is placed at the 3' end of an oligonucelotide, while the 5'-derivization provides the correct orientation for an oligonucleotide linked at the 5' end.

In another preferred embodiment, linker conjugation is achieved by the attachment of 4-mercaptobenzoic acid with a 5' pendant alkyl-amine or the incorporation of a short alkanethiol linker to the 3' end of DNA using a commercially-available reagent. These linkers give rise to more intervening σ-bonds between the gold surface and the DNA base stack, and can be used in when a more insulating linker is desired, such as for example, in the construction of a single-electron transistor of the invention.

Assembly and Wiring of DNA Arrays

Figure 8A:
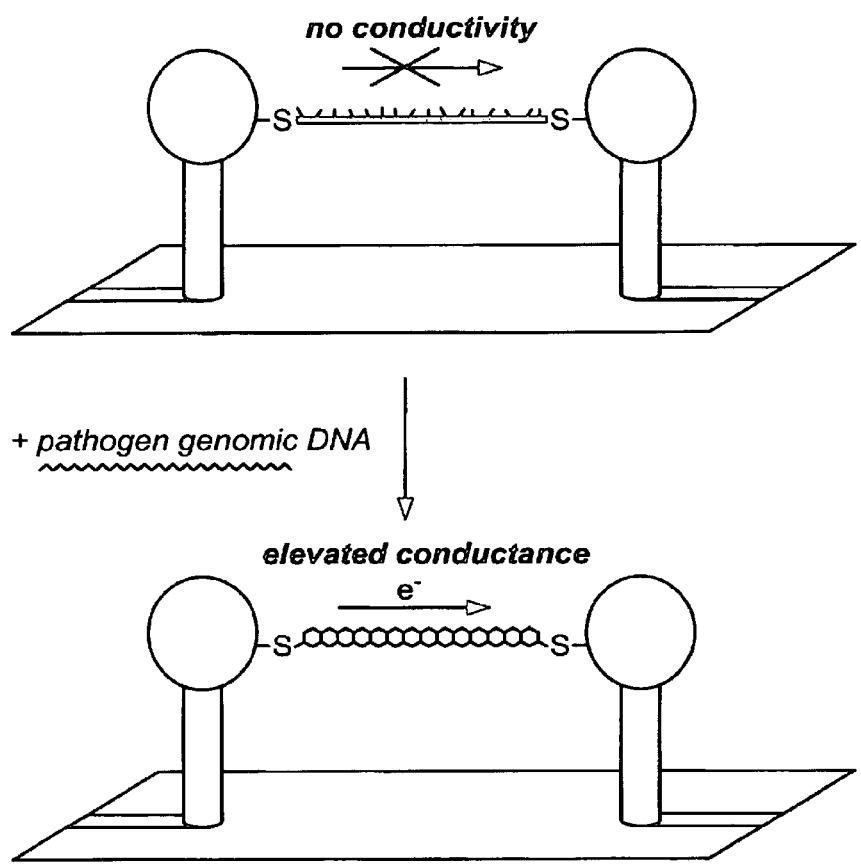
FIG. 8 shows two different configurations of the DNA-based biosensor of the invention for detection of the presence of a pathogenic agent, (a) based upon a strand that links adjacent gold spheres and (b) based upon two different sensor strands on adjacent spheres. In each case, hybridization completes the electrical circuit between the spheres.
Figure 8B:
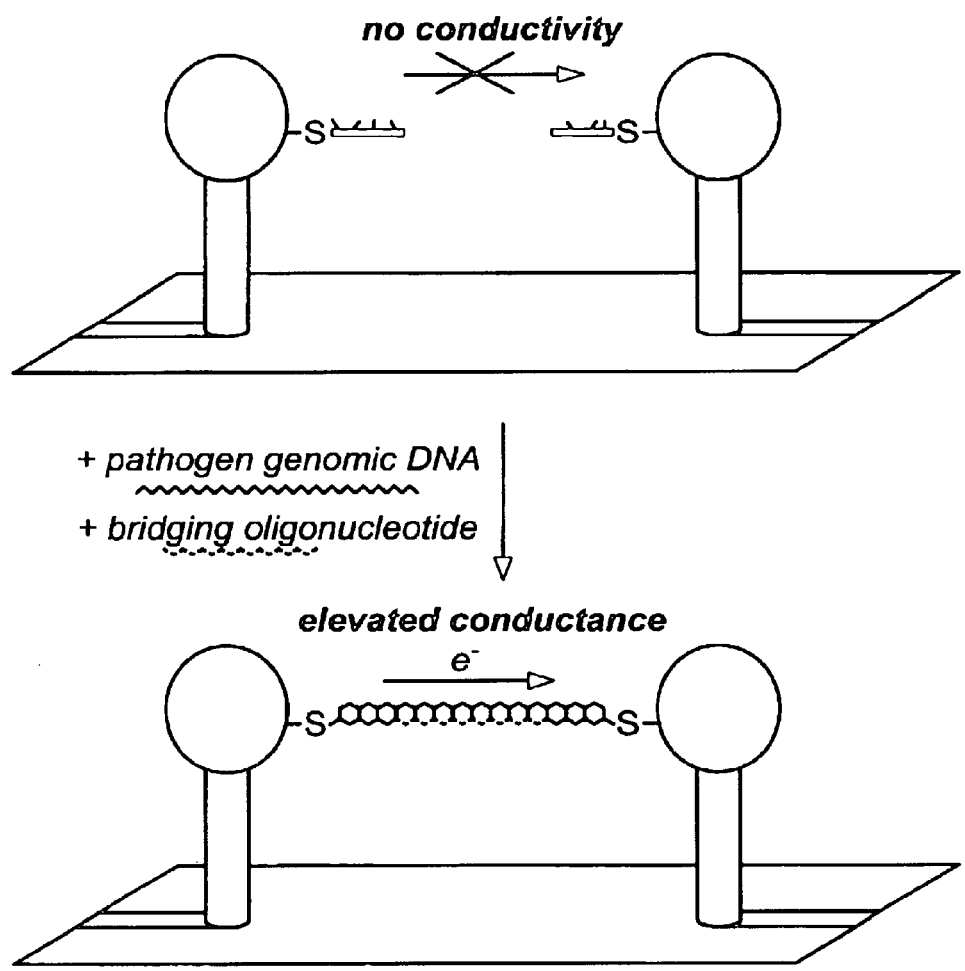
Figure 9B:
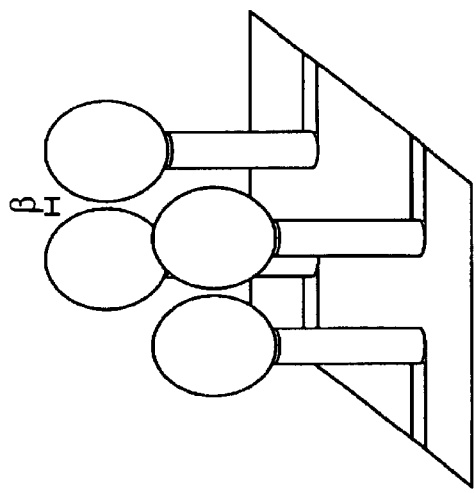
FIG. 9 shows the fabrication and wiring of DNA-CNT arrays of the invention where (a) ends electrically addressable nanotubes are etched and functionalized with thiols (b) subsequent self-assembly of gold-coated spheres to the nanotubes and (c) direction of DNA sequences with thiol linkers to selected spheres by application of voltage to produce an addressable array of goldbound DNA sequences.
Figure 9A:
Figure 9A:
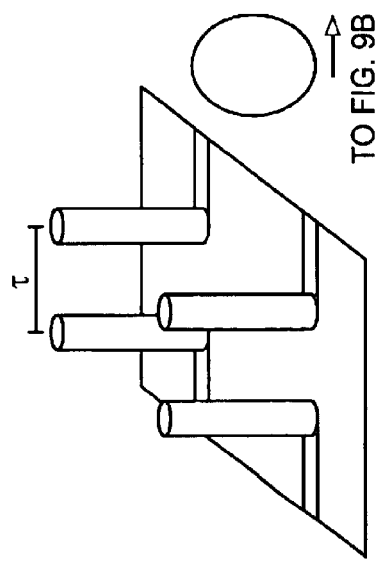
Figure 9C:
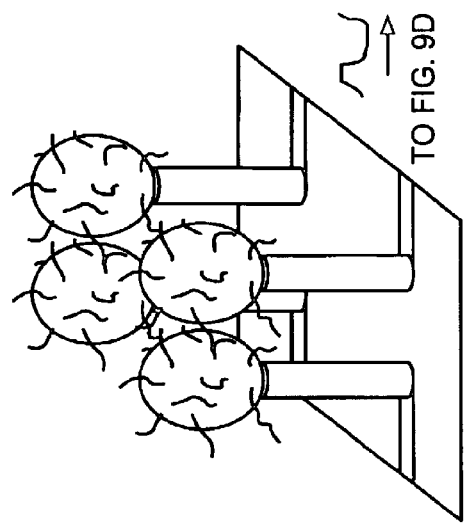
Figure 9D:
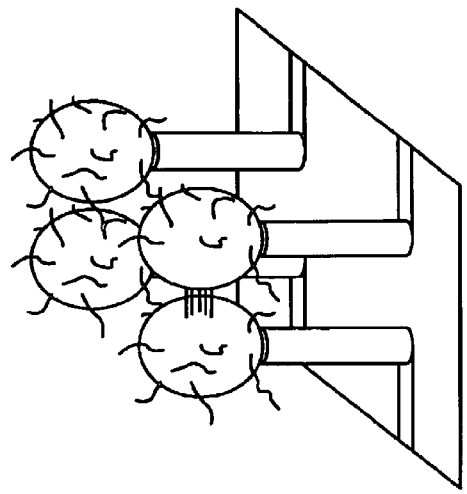

Assembly of "self-wiring" DNA arrays of the invention in which all of the CNTs are electrically addressable is shown in FIG. 7. The assembly process utilizes the array of electrically addressable CNTs prepared by methods of the invention described previously. In a preferred embodiment, the catalyst plug at the end of the CNTs is removed by etching the nanotubes in a combination of nitric and sulfuric acids, which in turn, leaves free carboxylic-acid groups at the ends of the nanotubes. The electrical contacts to the nanotubes are protected from the acids during the etching step. The carboxylic-acid groups at the nanotube ends are then be reacted with electrically conductive, thiol group containing compounds, such as for example, p-aminothiophenol, utilizing standard amide-coupling chemistry. Gold nanoparticles or gold-coated spheres are then self-assembled to the ends of the tubes (FIG. 8).

The assembly of the CNT array is completed by one of two different synthetic approaches. In a preferred embodiment, gold-coated spheres with pre-deposited single-stranded DNA sequences are attached selectively to the CNTs. The negative charge of DNA molecules, enables control of the attachment of spheres with a given DNA sequence to CNTs chosen electrically. For example, negatively-biased nanotubes do not bind the gold beads, whereas positively-biased nanotubes do. By sequential controlling the self-assembly reaction with beads containing different DNA sequences, predetermined DNA-CNT arrays can be fabricated.

In another preferred embodiment, the DNA is bound to gold-coated spheres after the spheres are attached to the CNTs in the array. This method provides post-attachment ability to adjust the spheres sizes. Sphere sizes can thus be reduced via acid etching or increased via electroless deposition. After spheres are attached to the nanotubes, potential differences are used to control selective attachment of single-stranded DNA sequences to spheres containing thiol linkers. In particular, self-assembly of the negatively-charged DNA to the spheres occurs readily under positive bias, but not under sufficient negative bias. FIG. 9 shows a schematic illustration of the process.

After assembly of the DNA-CNT arrays is complete, "wiring" a pair of neighboring spheres together is accomplished by subjecting the array to single-stranded sequences that are complementary to the different sequences on the two spheres. Hybridization completes the circuit between the beads. Although significant conductivity may be observed even for one double-stranded DNA connection between two beads, each connection is likely to be composed of hundreds of individual wires. The DNA-CNT arrays of the invention can be characterized by atomic force microscopy using standard analytical methods.

First Generation DNA-CNT Array Devices

Figure 10:
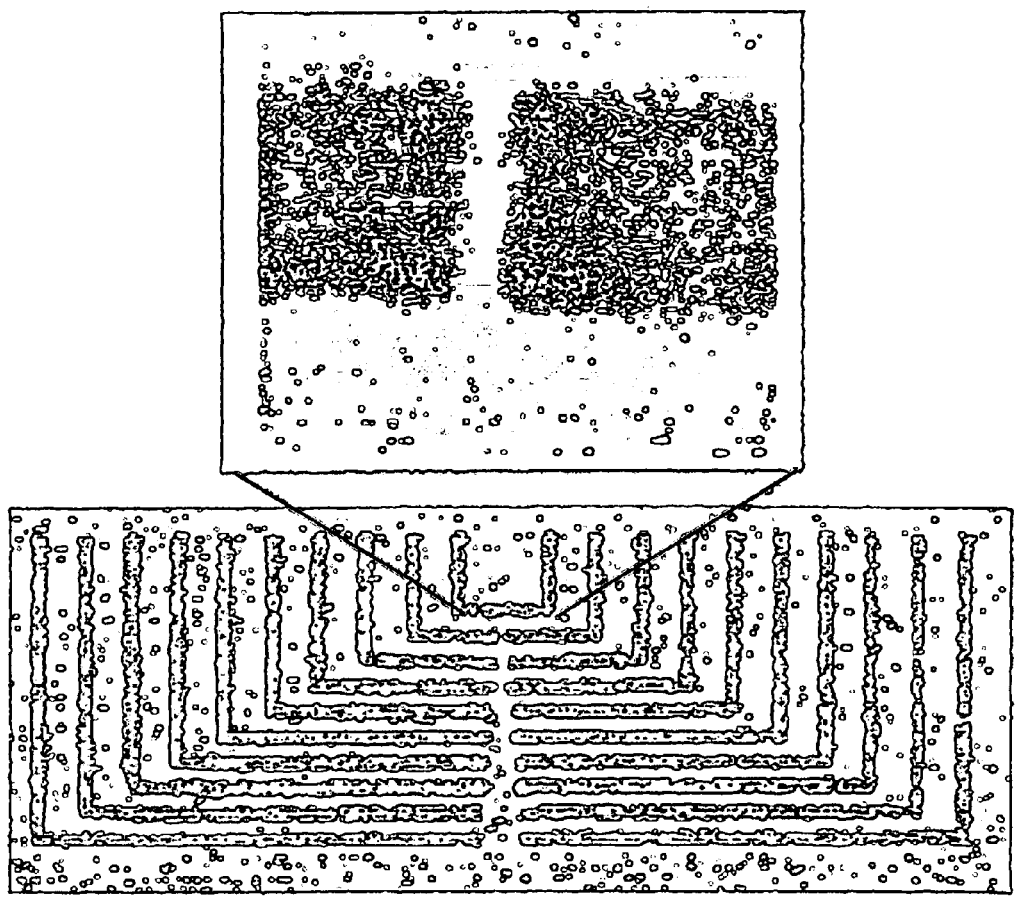
FIG. 10 shows nanowires (about 210 nm wide Cr on Si) with sepration gaps varying from about 10 nm to about 800 nm.

First generation of devices of the invention enables optimization of the fabrication, wiring and assembly procedures of the DNA-CNT arrays, and characterization of the electrical properties of DNA. First generation devices consist of two parallel rows of electrically-addressable nanotubes with spheres containing various single-stranded DNA sequences assembled to the ends (FIG. 10). Arrays are designed to enable optimization of the following:

Device Fabrication:

Optimization of reproducibility and fidelity of the CNT arrays that host the DNA, can be accomplished by seeking the most appropriate set of parameters for subsequent DNA strand attachment. Simple arrays of pairs of gold wires on silicon (specifically, about 70 nm gold (Au) atop about 10 nm titanium (Ti), on an approximately 90 nm silicon nitride ($Si_3N_4$) LPCVD-grown layer on silicon (Si) is preliminarily used. These are first defined by conventional (UV) photolithographic techniques in a Au-wire pattern of that will include the appropriate placement marks for the subsequent e-beam lithography step, wherein pairs of smaller Au wires can be defined, leading from the initial macroscale wires toward each other in the center of the wafer. The separation gap d between the termini of these leads can be initially varied in this first generation device from about several hundreds of nm to about the 50 to 100 nm range. As shown in FIG. 10, this is followed by a second e-beam lithography stage that defines the positions of the nickel or cobalt catalyst sites placed at the ends of the gold nanowires.

Device Assembly:

Determination of the appropriate voltages for directing the self-assembly of Au-coated spheres onto selected nanotubes is essential for device assembly. Due to the enhanced electric field at the tips of the nanotubes, these voltages are likely to vary with the diameters and lengths of nanotubes. Likewise, it is necessary to optimize the conditions under which DNA can be deposited on selected spheres with the desired efficiency and reproducibility. Selective tagging and fluorescence microscopy is used to characterize the arrays at each step of the device assembly procedure. For instance, to determine the positions of the gold spheres, a thiol-containing fluorophore, such as the product of the reaction of dansyl chloride with p-aminothiophenol, is used to "stain" these portions of the device selectively. Similarly, fluorescently-tagged sequences of complementary DNA is be used to determine the positions of each specific sequence that has been included in the array. Additionally, fluorescently-labeled bridging sequences and/or fluorescent probes that bind specifically to duplex DNA is employed to confirm that the desired "wiring" pattern has been achieved upon the addition of the bridging sequences.

Electrical Properties of DNA:

In a photoinduced charge transfer between DNA bases, a path that is restricted to one strand of the DNA double helix prompts the most efficient transfer. Electron migration across the hydrogen-bonded strands slows rates of charge transfer and increases the dependence of the rate of electron transfer on distance.

Figure 11:
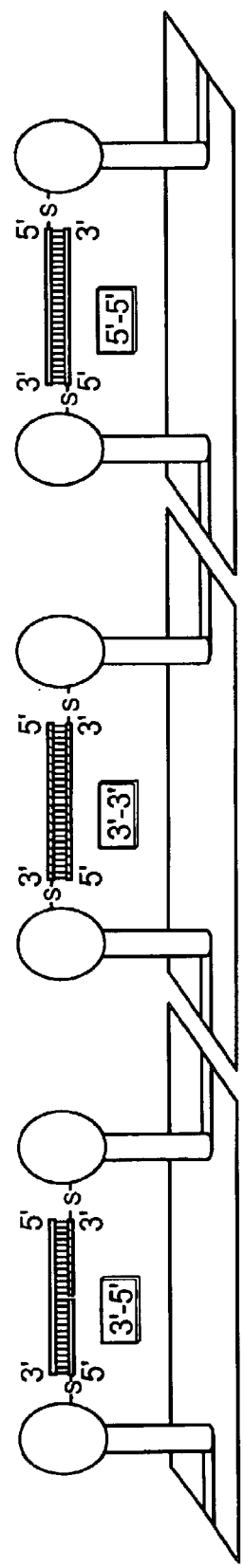
FIG. 11 shows assemblies with different gold-DNA connectivities.

The device of present invention contains individual single strands of DNA that are attached to nanoelectrodes, whereby the contacts may be varied to determine whether both ends of an individual DNA strand involved in a bridging double-stranded helix must be in electrical contact to obtain efficient conduction (FIG. 11). Furthermore, devices of the invention can be tested in two assembly types (i) assemblies featuring one DNA strand attached to two gold nanospheres through Au—S linkages at both the 3' and 5' ends of oligonucleotides comprising the same strand. The complementary strand is then attached only through non-covalent interactions (these assemblies will be referred to with the abbreviation 3'-5'), and (ii) assemblies featuring one end of each strand of the double helix attached to gold (abbreviated as either 3'-3' or 5'-5'). Higher levels of conductivity observed for the 3'-5' assembly indicate that electron flow along one side of the double helix is most efficient. Comparable conductivities for the 3'-5', 3'-3', and 5'—5' assemblies indicate that electron flow proceeds through the double helix as a whole.

Figure 12:
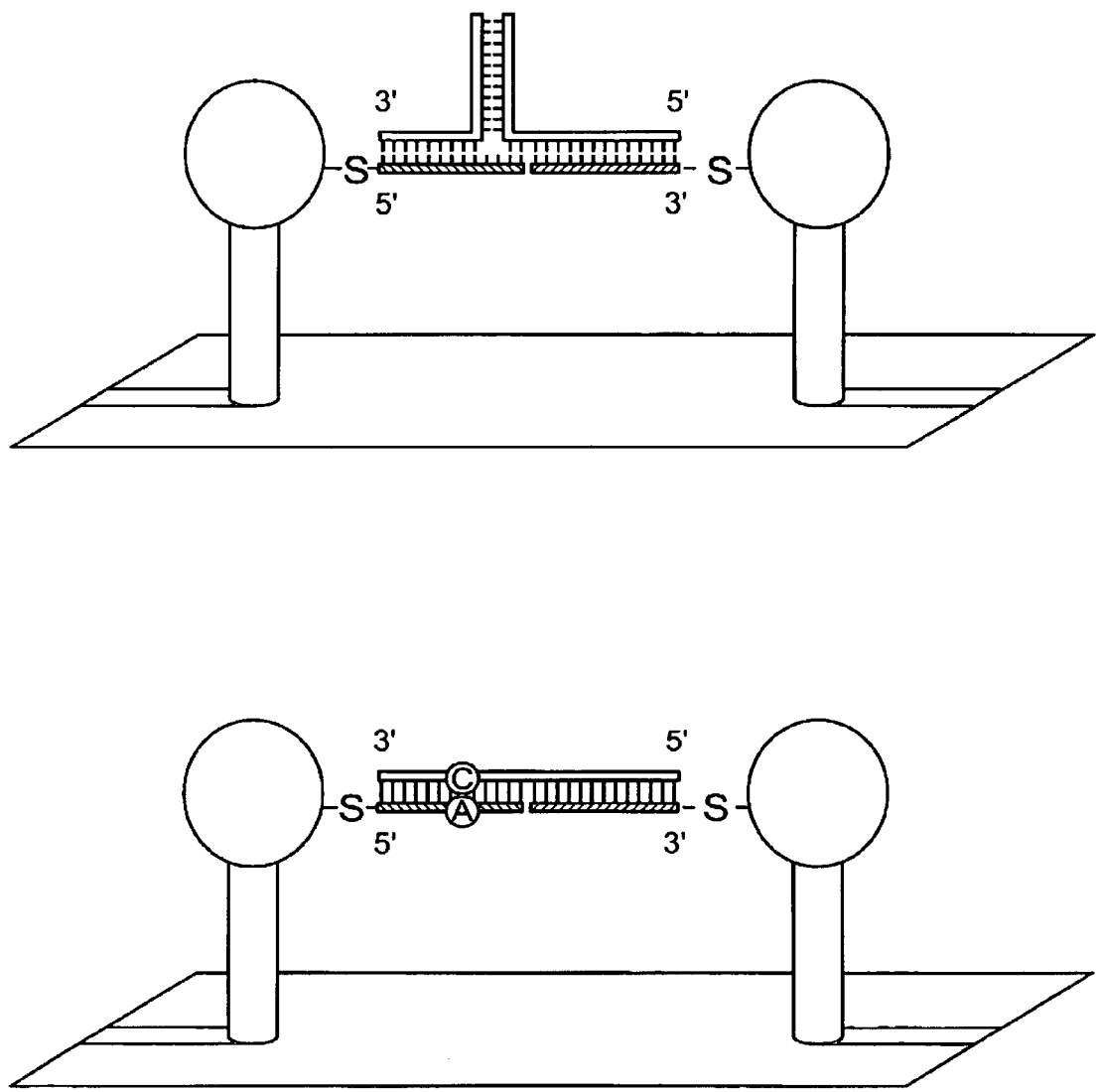
FIG. 12 shows the introduction of perturbations in base stacking for determination of conduction pathway and isolation of an intra-strand conduction path.

Base-pairing and Perturbations in Base Stacking:

This method helps establish that the currents observed are DNA-mediated in the device of the invention. FIG. 12 shows the perturbations introduced in base stacking within the double helix as a means of interrupting the conduction path. Since electron transfer between molecular donors and acceptors mediated by DNA shows that electronic coupling is severely attenuated in the presence of single-base mismatches that disrupt the integrity of the π-stack. The effects of mispaired bases on the conductivity-based assay can therefore, be measured.

It is desirable to limit the conduction path to one strand of the double helix. This is accomplished by engineering Au—S connectivities as described previously for the 3'-5' assembly, whereby intrastrand conductivity can be forced by disrupting the stacking in the strand that is not covalently linked to the gold microspheres. As shown in FIG. 12, disrupting the base stacking only in one strand can potentially be accomplished through the incorporation of 3-way helical junction, or by base mismatches perturbing stacking of the bases such as, for example, in a pyrimidine rich strand over a purine-rich strand. Systematic control over the path of current flow through DNA molecules can be therefore, utilized to design molectronic devices with specific performance requirements.

DNA Length:

DNA conductivity in the device of the invention is performed with first-generation CNT arrays by systematic variation of the length of the DNA sequence serving to bridge two nanotubes. In a preferred embodiment, the nanotube spacing is engineered at the level of catalyst deposition, that allows variations in spacing from about 10 nm to about 210 nm. In another preferred embodiment, the size of the capping gold micro-spheres is varied, thereby allowing spacing variations to less than about 10 nm. This distance range permits conductivity measurement in sequences of ranging from 30 to 500 base pairs.

DNA Sequence:

DNA bases vary significantly in redox potential. The purine bases exhibit electrochemical reduction potentials (versus nickel hydride electrode (NHE)) of $-2.8$ V (G) and $-2.5$ V (A), and oxidation potentials of $+1.5$ V (G) and $+2.0$ (A). The pyrimidines are more easily reduced than the purines ($-2.4$ V (C) and $-2.2$ V (T)), but are more difficult to oxidize ($+2.1$ V (C) and $+2.2$ V (T)). These differing potentials give rise to detectable effects in the conductivity of DNA molecules of different sequences.

The method of the invention employs the synthesis and immobilization DNA sequences of varying composition to measure conductivity variations. The ability to effectively "shut down" one strand of the DNA helix by manipulating connectivity or by introducing base-stacking perturbations in the devices of the present invention. For example, if conductivity relies only on the bases within one strand, a sequence composed only of cytidine and thymine can be compared to one containing only guanine and adenine. If conduction cannot be limited to an intrastrand pathway, sequences containing only GC base pairs can be examined and levels of conduction to sequences containing only AT base pairs can be compared.

In a preferred embodiment, unnatural bases are incorporated into bridging DNA sequences. For example, the higher electron affinity of 5-iodo-cytosine or the lower electron affinity of 5-methyl-uracil alters the voltage-current profiles obtained. The conductivities of sequences of varying composition are evaluated and correlated with the values obtained with the electronic properties of the intervening monomers, thereby enabling engineering of variations in bridging sequences that will provide molecular resistors, diodes and transistors. In another preferred embodiment, silver-coated DNA is used to provide highly conductive connections.

Second-generation DNA-CNT Array Devices

Optimization of first generation parameters in the devices of the invention enables the fabrication of complex circuit elements based on DNA-bridged nanotubes, such as resistors, capacitors, diodes and transistors. For resistors, necessary control required for the design and fabrication resistors over a wide range of resistance can be accomplished. Given the relation $R=\rho l/A$ (where $R$=resistance, $\rho$=resistivity, $l$=length and $A$=area), resistance can be varied through variations in: (i) $l$, by controlling the length of the bridged DNA strands (i.e. varying the separation between nanotubes) (ii) $A$, by controlling the number of double-stranded connections between nanotubes; or (iii) $\rho$, by choice of appropriate base sequence (and redox potential) within a connection. In addition, the base stacking pertubations described above can be intentionally employed as defect sites to control (increase) the electrical resistance across a path. Similarly, diodes can be created by choosing sequences with an appropriate spatial ordering of bases with different reduction potentials.

Figure 13:
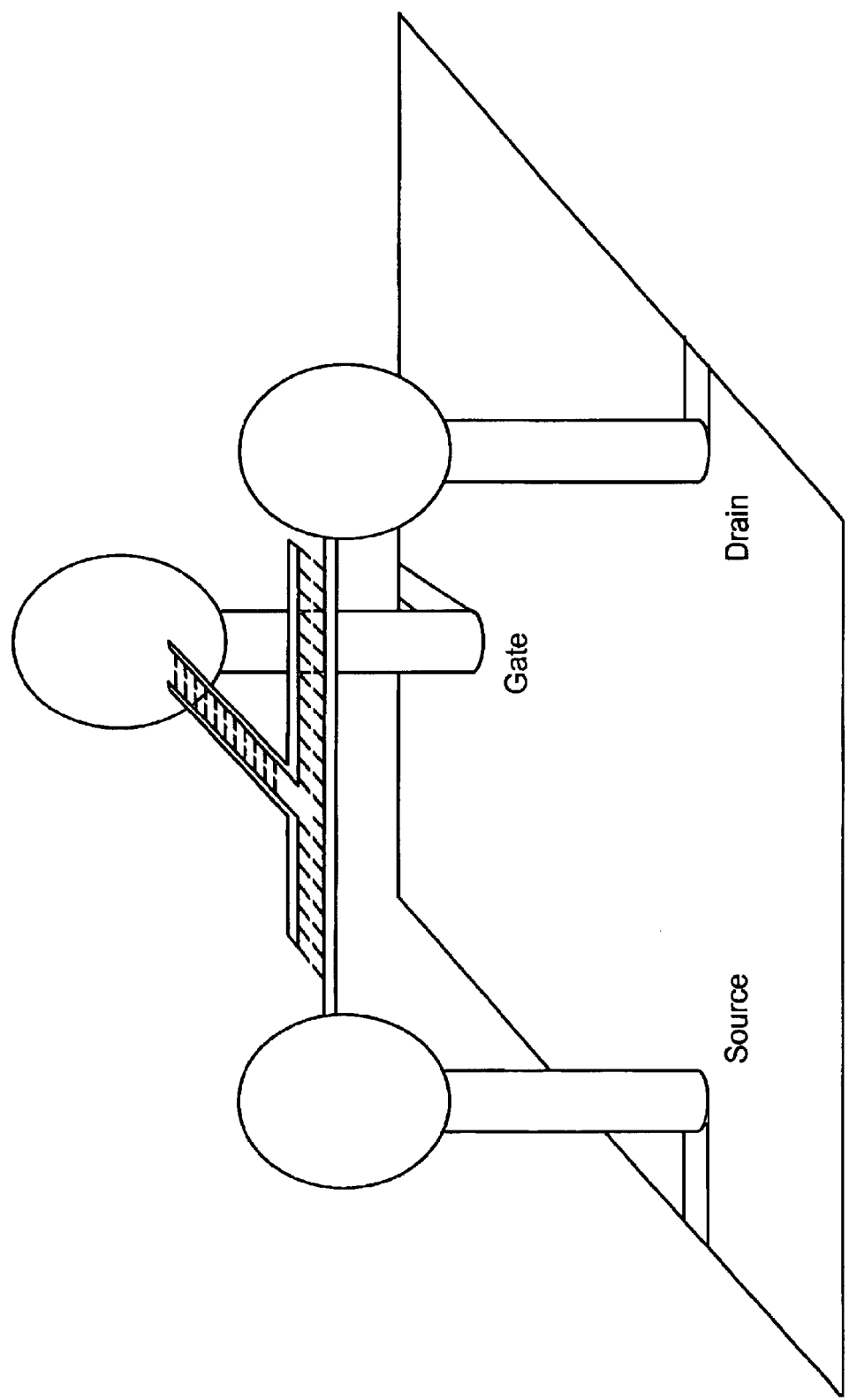
FIG. 13 shows a schematic of a second-generation device of the invention comprising a DNA-based FET.

A preferred embodiment of a nonlinear nanoscale devices (such as diodes and transistors) of the present invention is shown in FIG. 13. A pair of CNTs linked by a specific DNA sequence act as the source and drain of a 3-terminal FET (field-effect transistor). The controlling gate terminal is connected to the source/drain sequence by the formation of a three-way junction. When the bases across from the junction in the source/drain strand will remain stacked, bases with a high reduction potential may be placed in these positions, such that this potential can be modulated by placing a voltage on the gate. On the other hand, if base stacking is lost in this region, synthetic bases that can then be aligned (and therefore stacked) in an electric field may be chosen. In either case, voltage applied at the gate enables control of current along the source/drain path.

In another preferred embodiment, the device of the invention is a single electron transistor (SET), wherein the main conduction process is by electrons tunneling across a tunnel barrier. FIG. 7 shows thiol linkers between a metal sphere atop the nanotube tip and the DNA strands. By altering the chemical structure of these linkers (as shown in FIG. 2), the electron transport across these linkers can be tuned from conducting to insulating. In the non-conducting configuration, these links act as tunnel barriers between metallic contacts and the DNA, and perform the electron sensing function by themselves. The source and drain remain as shown in FIG. 13, but the gate electrode is not required. This results in new types of molectronic SET that function at room temperature, improved photon sensors, including in the ultraviolet, visible and infrared ranges, and Coulomb-blockade devices with a tunable negative differential resistance.

Third Generation DNA-CNT Arrays

Third-generation devices of the invention enable the fabrication of entire functional circuits. As shown in FIG. 12, an important prerequisite in such circuits is ability of DNA to "wire" spheres on CNTs that are not initially electrically addressable, thereby allowing the creation of complete, self-wiring circuits.

Figure 14:
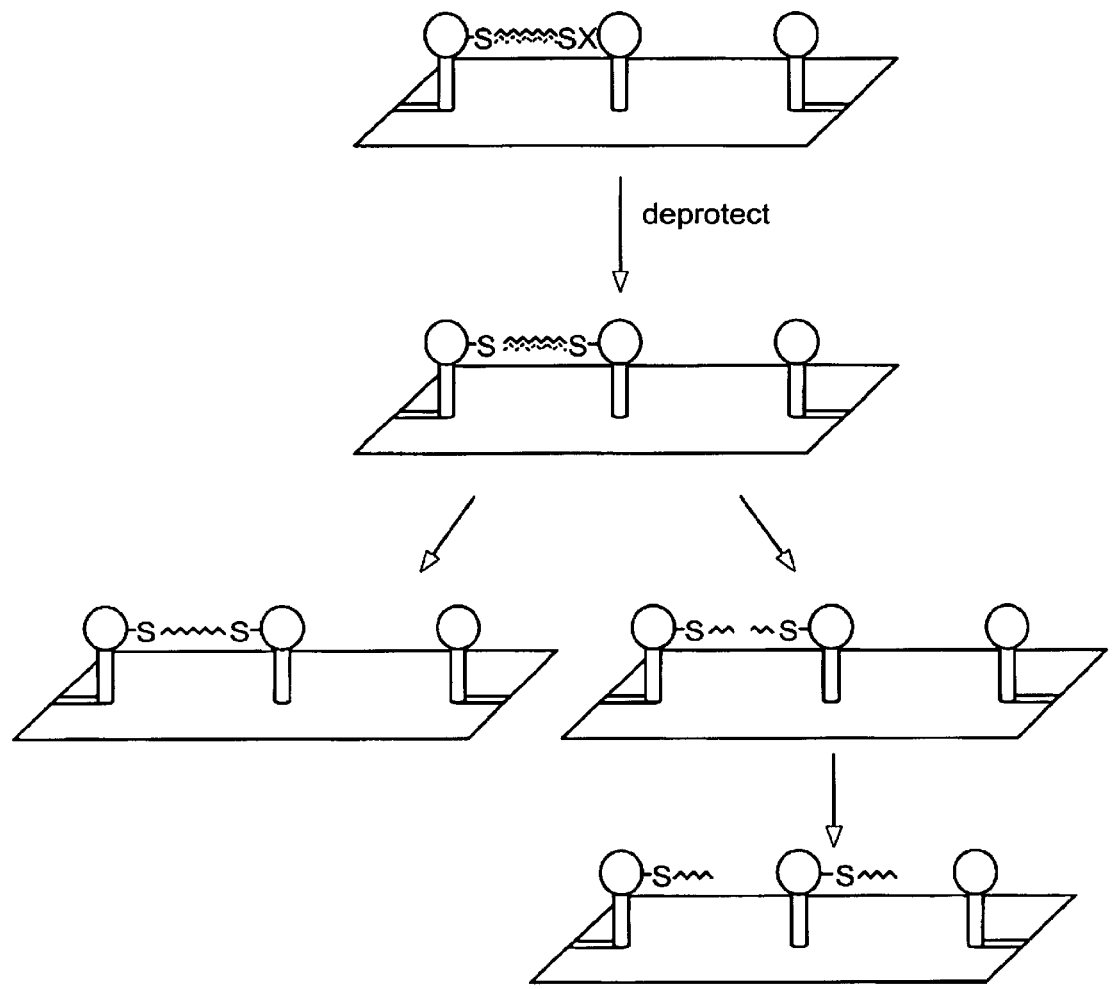
FIG. 14 shows a scheme for attachement of DNA to spheres that are electrically non-addressable.

FIG. 14 shows a schematic representation of a preferred embodiment, wherein DNA strands with a free thiol at one end and a chemically-protected thiol at the other that are attached to an electrically-addressable sphere. To ensure the rigidity of these sequences, duplex DNA is used to preclude the strands from becoming hybridized with a complementary strand after attachment to the sphere. Subsequent chemical deprotection of the thiols at the unattached ends of the strands now permits them to attach to an unaddressed sphere that is within a proper distance of the sphere of initial DNA attachment. At this point, the complementary strand is removed by thermal or chemical methods. If further connections to the unaddressed sphere are not required, then the single-stranded connection is retained as such, since the base-stacking necessary for conductivity occurs only in the presence of a complementary strand. On the other hand, to make further connections to this nanotube, a restriction enzyme can be used to cut the strand at a predetermined position. Diffusion of linking thiols along the surfaces of the spheres will lead to an isotropic distribution of DNA around the unaddressed sphere over time. Ligation of an appropriate sequence to the DNA on the unaddressed sphere allows for repetition of this to form connections to another unaddressed spheres.

Fourth-generation DNA-CNT Arrays

Figure 15:
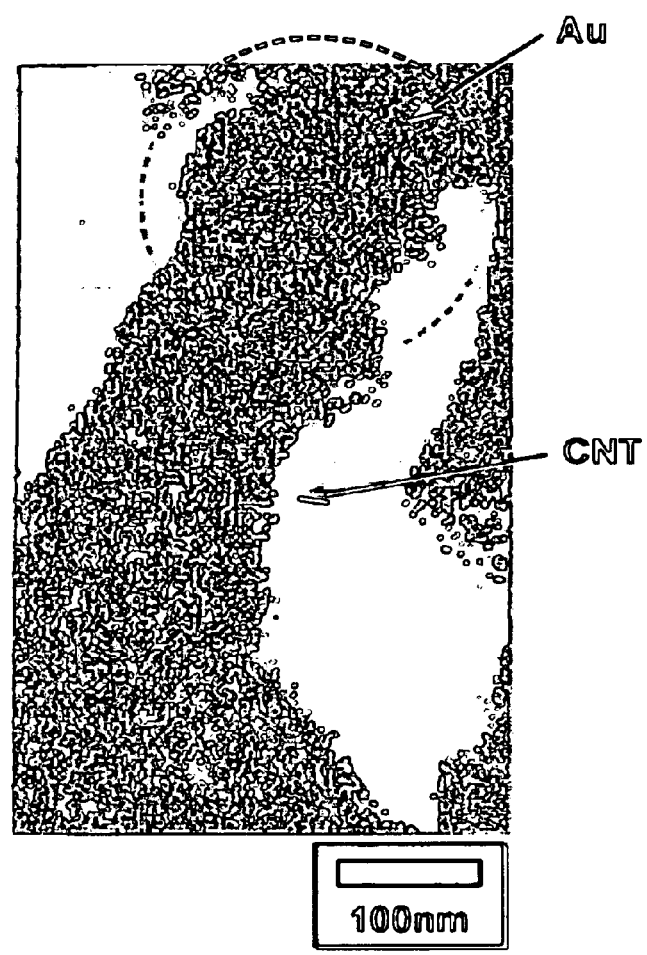
FIG. 15 shows an SEM photomicrograph of a gold nanoparticle attached to the tip of a multi-walled CNT (both having a nominal diameter of about 121 nm) by the method of the invention.

The fourth generation of devices of the invention combine all of the advances made in the previous three generations, while providing the ultimate degree of miniaturization. It enables fabrication of arrays of closely-spaced, electrically addressable single-walled CNTs of fixed chirality (i.e., conductivity). In a preferred embodiment, gold-coated spheres are replaced by monodisperse gold nanoparticles with diameters from about 10 nm to about 200 nm. The attachment of gold nanoparticles of controlled size to single-walled CNTs is essential the fourth-generation device technology of the invention in order to reach an appropriate level of miniaturization. FIG. 15 shows a gold nanoparticle about 121 nm in diameter attached to a multi-walled CNT of nominal diameter about 121 nm.

The factor that determines optimal feature size in such a device is the number of base pairs needed in a strand of duplex DNA to prevent melting under ambient conditions. At room temperature, this number is approximately 15, which requires to a minimum interconnect size of about 5 nm. Practically, however, slightly longer sequences are employed to ensure availability of adequate sequence diversity to make a large numbers of unique, independently "wirable" connections. It is, therefore, possible to fabricate complex, self-wiring circuits with interconnect lengths on the order of about 15 nm and terminal sizes on the order of about 10 nm, which is sustantially smaller than those obtained by current silicon-based lithographic techniques. In addition to the unique capabilities of the DNA-based electronic devices of the previously described generations of the invention, fourth-generation devices additionally offer significantly faster operation than standard microcircuits.

Conductivity-based DNA-CNT Sensor Device for Microorganism Detection

A sensor device of the present invention can be used for detecting DNA sequences found in the genome of pathalogical microorganisms, such as for example, *Bacillus anthracis* (anthrax), a lethal pathogen that is a dangerous agent because of facile dissemination through aersolization (FIG. 16). In a preferred embodiment a 150 nucleotide fragment of the genome of *B. anthracis* identified as a unique maker for this species is used in the analysis. A 50-nucleotide region of this fragment can be targeted that is sufficiently unique to "report" the presence of the species with a high degree of accuracy. Two adjacent CNTs can be bridged with a thiol-modified 50-base pair synthetic oligonucleotide that is complementary to the target sequence. Detection of the presence of the anthrax sequence can then be performed in the simplest possible sample, a purified 50-mer generated synthetically that corresponds to the target genomic sequence. The levels of conductivity in the presence and absence of the target sequence can be monitored to first establish that a differential response can be acquired. Based on known electronic properties of DNA, introduction of the complementary target sequence will present a molecular bridge with conductivity significantly elevated over the single-stranded bridge. Once this measurable conductivity increase resulting from the presence of the target strand is established, it will determine the detection limits for the DNA-CNT array sensor device of the invention, and monitor the kinetics of the hybridization events. Such analyses can be conducted under artificially simplified conditions to enable establishment of assay viability and for optimizing sensitivity.

In another preferred embodiment, the complexity of analyte sample is increased by using DNA produced in bacterial culture. The complete 150 nucleotide anthrax marker fragment previously identified is introduced into a plasmid that can be produced in *E. coli*. The presence of the targeted sequence in lysates containing different cell densities that will thereby contain different levels of plasmid DNA is assayed. This allows protocol optimization in the presence of other DNA sequences and other components present in cellular extracts. Plasmid constructs are generated such that they incorporate larger segments of the anthrax genome in order to establish the effect of overhanging, non-hybridized sequences, or to encode similar regions of nonvirulent, closely-related species for establishing the ability of the sensor to discriminate against innocuous bacteria. After detection of DNA sequences with high accuracy and sensitivity is optimized, the sensor device of the invention is used in field testing for anthrax.

The devices methods and processes of the invention can be used in biological sensing devices to sense and detect pathological biological species including microorganisms (such as anthrax), viruses, pathogenic biological molecules (such as toxins), enzymes, proteins, and chemical agents at extremely low levels with high specificity. The present invention can also be used to fabricate multi-element DNA circuits for applications such as amplification, logic, and memory circuits. Additionally, such devices also allow the evaluation of the speed and performance of DNA-based circuitry. Potential applications of such circuits include sensors for specific DNA sequences with single-molecule sensitivity and DNA-based computers in which a DNA amplification step is not required.

The devices of the invention, including mechanical and chemical processes for their preparation, as well as methods their fabrication will become apparent to one familiar in the art based on the aforementioned embodiments and the following non-limiting examples.

EXAMPLE 1

Controllable Creation of Arrays of Addressable Multi-walled Carbon Nanotubes

CNTs are grown by the plasma-enhanced hot filament chemical vapor deposition method, including on an e-beam patterned substrate. Metallic nickel, deposited via e-beam lithography over a non-catalytic metal provides the electrical leads, is used as the catalyst for CNT growth.

EXAMPLE 2

Growth of Controlled Dimension Gold-coated Spheres

Gold-coating procedure of spheres utilizes the functionalization of microspheres with thiols groups to enable the self-assembly of metallic gold nanoparticles on functionalized sphere surfaces. The initially formed gold layer is subsequently built up either through sequential steps of linker addition followed by additional contact with gold nanoparticles, or through electroless deposition of gold on the functionalized sphere surfaces.

EXAMPLE 3

Synthesis of DNA Sequences with Thiol Linkers

The synthetic method involves a solution-phase reaction between 4-mercaptobenzoic acid and a terminal amine either at the 2' or 5' position on the ribose moiety. The incorporation of an amine at the 2' or 5' position is accomplished during chemical DNA synthesis using commercially available reagents. A 2'-derivatization is carried out to orient the DNA away from a gold surface when the linker is placed at the 3' end of an oligonucelotide, while a 5'-derivization is done to orient the oligonucleotide linked at the 5' end. Alternatively 4-mercaptobenzoic acid is reacted with a 5' pendant alkyl-amine or the incorporation of a short alkanethiol linker to the 3' end of DNA using a commercially-available reagent.

EXAMPLE 4

Fabrication of Electrically-addressable Carbon Nanotube Arrays

The preliminary step involves a micro- and nanolithographic preparation of CNT catalyst sites and metallic addressing wires on single crystal silicon wafers. This is followed by growth of aligned CNTs via hot filament, plasma-enhanced chemical vapor deposition (PECVD). A series of thin gold wires lithographically on the silicon is defined, with the inner ends of pairs of individual wires in very close proximity (~100 nm). At these proximal ends, a CNT growth catalyst (e.g., Ni or Co) nanodot site is defined using e-beam lithography, and the catalyst material deposited. This wafer is then placed in the CVD chamber, with subsequent CNT growth occurring only at the catalyst nucleation sites. At this point the gold wires may be passivated using electropolymerization. If deemed necessary, additional steps can be introduced to obtain strictly uniform height of the CNTs in the arrays. Depending on growth conditions used, CNTs height in an array in a given growth run can be varied in height by 10%–50% Height uniformity is accomplished by performing additional mechanical polish steps.

EXAMPLE 5

Catalyst Deposition Methods

Conventional e-beam evaporation of nickel (Ni) or cobalt (Co) is used after an e-beam lithography step is performed on the substrate to define the catalyst sites in an e-beam resist. This is followed by a lift-off step (of the unwanted catalyst material), leaving only the Ni or Co nanodots on top of the gold leads. Alternatively, a self-assembly of catalyst nano-particles from a catalyst-containing solution is used, which precludes the need for the lift-off step. In either case, at the end of this phase, electrically addressable pairs of CNTs with well-defined heights and lateral separations are prepared. Separations between nanotubes down to 10 nm, can be obtained reproducibly by these methods.

EXAMPLE 6

Assembly and Wiring of DNA-CNT Arrays

The catalyst plug at the end of the CNTs array of electrically addressable CNTs obtained in Example 4 is removed by etching the tubes in a combination of nitric and sulfuric acids, to give free carboxylic acid groups at the ends of the CNTs. The electrical contacts to the tubes are protected from the acids during the etching step. The carboxylic-acid groups at the ends of the tubes are then be reacted with p-aminothiophenol using standard amide-coupling chemistry. Gold nanoparticles or gold-coated spheres are then self-assembled to the ends of the tubes, following which single-stranded DNA is deposited on the coated spheres. The gold-coated spheres with predeposited single-stranded DNA sequences are then attached selectively to the CNTs. By a sequential control of self-assembly reactions with beads containing different DNA sequences, desired array can are fabricated. Alternatively, the DNA is bound to the gold-coated spheres after the spheres have been attached to the CNTs in the array. The sizes of the spheres are then adjusted if necessary, after attachment via acid etching (if smaller spheres are required) or electroless deposition (if larger spheres are required). Once the spheres have been attached to the CNTs, potential differences are used to control selective attachment of spheres single-stranded DNA sequences with thiol to other spheres.

CNT-supported DNA arrays of the present invention can be used in the development of a new class of sensors that differ from those currently available in the degree of portability and sensitivity. Many of the current methods for pathogen detection require the amplification of DNA samples using the polymerase chain reaction (PCR), a powerful but target-specific and time-consuming process. The nanoscale detector of the present invention is expected to be effective at very low concentrations of DNA and may enable the direct analysis of aerosolized agents collected from air. The transport of charge through DNA, it assays an intrinsic property of DNA, not one imparted by a probe molecule and hybridization thermodynamics. This feature will provide greater sensitivity and accuracy.

What is claimed is:

1. An electrically conducting carbon nanotube array comprising:
   a) at least one pair of carbon nanotube tubules each having a proximal end and a distal end, said proximal ends attached to a substrate;
   b) a metallic material attached to at least a portion of the carbon nanotube tubules including the distal end; and
   c) an electrically conductive biological compound attached to the metallic material, and provides electrical connectivity between the pair of nanotube tubules.

2. The electrically conducting carbon nanotube array of claim 1 comprising at least one pair of electrically conductive aligned nanotube tubules positioned proximally on a substrate surface such that their distal ends are bridged by the electrically conductive biological compound.

3. The electrically conducting carbon nanotube array of claim 1 wherein the nanotube tubule is a single wall or a multi-walled carbon nanotube.

4. The electrically conducting carbon nanotube array of claim 1 wherein the metallic material comprises at least one metal, an alloy or combinations thereof.

5. The electrically conducting carbon nanotube array of claim 1 wherein the metallic material is selected from the group consisting of gold, silver, platinum, copper, nickel, cobalt and aluminum.

6. The electrically conducting carbon nanotube array of claim 1 wherein the metallic material is gold.

7. The electrically conducting carbon nanotube array of claim 1 wherein the metallic material is located at the distal end of the nanotube tubule.

8. The electrically conducting carbon nanotube array of claim 1 wherein the metallic material is present as a surface coating on the carbon nanotube tubule.

9. The electrically conducting carbon nanotube array of claim 1 wherein the metallic material is present as a particulate at the terminal end of the carbon nanotube tubule.

10. The electrically conducting carbon nanotube array of claim 1 wherein the metallic material comprises a polymeric or glass bead wherein surface of said bead contains a metal deposited thereon.

11. The electrically conducting carbon nanotube array of claim 1 wherein the substrate is a non-metallic material.

12. The electrically conducting carbon nanotube array of claim 11 wherein the substrate is a an electrically semiconducting material.

13. The electrically conducting carbon nanotube array of claim 12 wherein the substrate is silicon.

14. The electrically conducting carbon nanotube array of claim 1 wherein the electrically conductive biological compound is chemically bonded to the metallic material.

15. The electrically conducting carbon nanotube array of claim 1 wherein the electrically conductive biological compound is immobilized on the surface of material via surface adsorption, ionic bonding, hydrogen bonding or covalent chemical bonding.

16. The electrically conducting carbon nanotube array of claim 1 wherein the electrically conductive biological compound includes a substituent selected from the group consisting of thiol, thiophenol, thiocarboxylic acid, carboxylic acid and disulfide.

17. The electrically conducting carbon nanotube array of claim 16 wherein the substituent is a thiol.

18. The electrically conducting carbon nanotube array of claim 1 wherein the electrically conductive biological compound is a nucleic acid, oligonucleotide, amino acid, enzyme, protein or segments or derivatives thereof.

19. The electrically conducting carbon nanotube array of claim 18 wherein the electrically conductive biological compound is a chemically derivatized nucleic acid, amino acid enzyme, protein or a segment thereof.

20. The electrically conducting carbon nanotube array of claim 1 wherein the electrically conductive biological compound is DNA, RNA, or segments or derivatives thereof.

21. The carbon nanotube array of claim 1 wherein the electrically conductive biological compound is single-stranded DNA, derivatized single-stranded DNA or segments or derivatives thereof.

22. A molecular sensor device comprising:
   a) an electrically conducting carbon nanotube array comprising at least two carbon nanotube tubules each comprising a proximal end and a distal end, said proximal ends attached to a substrate;

b) a metallic material attached to at least a portion of the carbon nanotube tubules including their distal ends; and c) an electrically conductive biological compound attached to the metallic material and provides an electrical contact between the carbon nanotube tubules.

23. The molecular sensor device of claim 22 wherein the carbon nanotube tubules are single walled or multi-walled.

24. The molecular sensor device of claim 22 wherein the metallic material comprises at least a one metal, a metallic alloy or combinations thereof.

25. The molecular sensor device of claim 22 wherein the metallic material is selected from the group consisting of gold, silver, platinum, copper, nickel, cobalt and aluminum.

26. The molecular sensor device of claim 22 wherein the metallic material is gold.

27. The molecular sensor device of claim 22 wherein the metallic material is located at the distal end of the carbon nanotube tubule.

28. The molecular sensor device of claim 22 wherein the metallic material is present as a surface coating on the carbon nanotube tubule.

29. The molecular sensor device of claim 22 wherein the metallic material is present as a particulate at the terminal end of the carbon nanotube tubule.

30. The molecular sensor device of claim 22 wherein the metallic material comprises a polymeric or glass bead wherein surface of said bead contains a metal deposited thereon.

31. The molecular sensor device of claim 22 wherein the biological compound is immobilized on the surface of material via surface adsorption, ionic bonding, hydrogen bonding or covalent chemical bonding.

32. The molecular sensor device of claim 22 wherein the biological compound is chemically derivatized to include a substituent selected from thiol, thiophenol, thiocarboxylic acid, carboxylic acid and disulfide.

33. The molecular sensor device of claim 32 wherein the substituent is thiol.

34. The molecular sensor device of claim 22 wherein the biological compound is a nucleic acid, amino acid enzyme or protein or derivatives thereof.

35. The molecular sensor device of claim 22 wherein the biological compound is a chemically derivatized nucleic acid, amino acid enzyme, protein or a segment thereof.

36. The molecular sensor device of claim 22 wherein the biological compound is selected from the group consisting of DNA, RNA, and segments or derivatives thereof.

37. The molecular sensor device of claim 22 wherein the biological compound is single-stranded DNA, denvatized single-stranded DNA or segments thereof.

38. The molecular sensor device of claim 22 that is capable of sensing and detecting microorganisms, viruses, toxins, proteins, nucleic acids, amino acids, enzymes and biologically active chemicals.

39. The molecular sensor device of claim 38 wherein the microorganisms are pathogenic bacteria, yeast or fungi.

40. The molecular sensor device of claim 39 wherein the microorganism is *Bacillus anthtracis* (anthrax).

41. The molecular sensor device of claim 22 wherein the electrical contact between the pair of carbon nanotube tubules provides electrical charge conduction.

42. The molecular sensor device of claim 22 wherein the biological compound interacts with a target species to produce a change in electrical conductivity in the sensor device.

* * * * *

UNITED STATES PATENT AND TRADEMARK OFFICE
CERTIFICATE OF CORRECTION

PATENT NO.       : 6,958,216 B2
APPLICATION NO.  : 10/042911
DATED            : October 25, 2005
INVENTOR(S)      : Shana Kelley et al.

It is certified that error appears in the above-identified patent and that said Letters Patent is hereby corrected as shown below:

Column 18, line 29, claim 12 should read:
12.    The electrically conducting carbon nanotube array of claim 11 wherein the substrate is an electrically semi-conducting material.

Column 20, line 15, claim 37 should read:
37.    The molecular sensor device of claim 24 wherein the biological compound is single-stranded DNA, derivatized single-stranded DNA or segments thereof.

Signed and Sealed this

Twenty-seventh Day of November, 2007

JON W. DUDAS
*Director of the United States Patent and Trademark Office*